United States Patent
Hirayama et al.

(12)

(10) Patent No.: US 6,221,864 B1
(45) Date of Patent: Apr. 24, 2001

(54) PROPHYLACTIC OR THERAPEUTIC AGENT FOR DISEASES ATTRIBUTABLE TO INFECTION WITH HELICOBACTERS

(75) Inventors: Fumihiro Hirayama; Mitsuharu Sano; Nobuhiro Sakurai; Yoshito Yokoyama, all of Fukuoka (JP)

(73) Assignee: Welfide Corporation, Osaka (JP)

( * ) Notice: Subject to any disclaimer, the term of this patent is extended or adjusted under 35 U.S.C. 154(b) by 0 days.

(21) Appl. No.: 09/446,662

(22) Filed: Dec. 23, 1999

(30) Foreign Application Priority Data

Jun. 23, 1997 (JP) .................................................. 9-165646

(51) Int. Cl.⁷ .................... A61K 31/5377; A61P 1/04; A61P 31/04
(52) U.S. Cl. ........................................ 514/235.2; 544/128
(58) Field of Search ......................... 544/128; 514/235.2

(56) References Cited

FOREIGN PATENT DOCUMENTS

| 63-264461 | 11/1988 | (JP) . |
| 2-138278 | 5/1990 | (JP) . |
| 7-188230 | 10/1995 | (JP) . |
| 8-48629 | 2/1996 | (JP) . |

OTHER PUBLICATIONS

Yokota et al, *Chemical Abstracts,* vol. 114, No. 228, 770, 1991.*

\* cited by examiner

*Primary Examiner*—Robert W. Ramsuer
(74) *Attorney, Agent, or Firm*—Wenderoth, Lind & Ponack, L.L.P.

(57) ABSTRACT

The present invention relates to an agent for the prophylaxis and treatment of diseases caused by Helicobacter infections, which comprises (S)-1-cyclopropyl-1,4-dihydro-7-[2-(N,N-dimethylaminomethyl)morpholino]-6-fluoro-8-methoxy-4-oxoquinoline-3-carboxylic acid or a pharmaceutically acceptable salt thereof. The prophylactic and therapeutic agent of the present invention is effective even when used alone in a small dose for a short time, is almost free of problematic side effects such as tolerance and diarrhea, and is low toxic and capable of safe and ensured bacterial eradication. It is useful for the prophylaxis and treatment of diseases caused by Helicobacter infections, particularly, gastritis, gastric ulcer, duodenal ulcer, malignant lymphoma and gastric cancer.

7 Claims, No Drawings

PROPHYLACTIC OR THERAPEUTIC AGENT FOR DISEASES ATTRIBUTABLE TO INFECTION WITH HELICOBACTERS

TECHNICAL FIELD

The present invention relates to a pharmaceutical agent containing (S)-1-cyclopropyl-1,4-dihydro-7-[2-(N,N-dimethylaminomethyl)morpholino]-6-fluoro-8-methoxy-4-oxoquinoline-3-carboxylic acid or a pharmaceutically acceptable salt thereof, which agent is useful for the prophylaxis and treatment of diseases caused by Helicobacter infections, particularly gastritis, gastric ulcer, duodenal ulcer, gastric malignant lymphoma and gastric cancer.

BACKGROUND ART

By the development of antisecretory drugs, such as histamine $H_2$ antagonist and proton pump inhibitor, peptic ulcers, inclusive of a number of ulcers that heretofore required an operation, can now be cured by drug therapy. In view of the fact that most of the ulcers once cured are subject to recurrence and relapse, however, a maintenance therapy over a long period of time is considered to be necessary even after a complete cure, and even during the maintenance therapy, recurrence and relapse are highly frequently observed.

In 1988, Marrshall B. J. et. al. (Lancet ii: 1437–42, 1988) applied eradication of Helicobacter pylori (H. pylori) to H. pylori positive gastric/duodenal ulcer cases, and reported a noticeable decrease in the relapse of duodenal ulcer. Thereafter in 1992, Graham D. Y. et. al. (Ann. Intern. Med. 116:705–708, 1992.) and in 1993, Hentschel E. et. al. (N. Engl. J. Med. 328:308–312, 1993) successively reported that relapse of peptic ulcer decreased significantly in the group subjected to eradication of H. pylori. Given the strong suggestion of the relationship between H. pylori infection, and gastritis and gastric/duodenal ulcer, a bacterial eradication therapy has been tentatively applied to patients with gastric/duodenal ulcer.

In February 1994, the United States National Institutes of Health (NIH) recommended that bacterial eradication therapy should be applied to duodenal ulcer and gastric ulcer, whether on first presentation with illness or recurrence (NIH Consensus Conference: Helicobacter pylori in peptic ulcer disease. JAMA 272:65–69, 1994), and in this year, WHO/IARC reported that H. pylori belonged to group 1 (definite carcinogenic substance) of gastric cancer (WHO International Agency for Research on Cancer. IARC monographs on the evaluation of carcinogenic risks to humans. Schistomsomes, Liver flukes and Helicobacter pylori. Lyon. 61, 177–241, 1994). This report suggests that the target of bacterial eradication therapy for H. pylori is spreading to the treatment and prophylaxis of gastric cancer and gastric malignant lymphoma (Personnet J. et. al., N. Engl. J. Med. 325:1127–1131, 1991, Uemura N. et. al., Gastroenterology 110:A525, 1996).

Considering from these standpoints, bacterial eradication therapy for H. pylori has been actively studied at present. The bacterial eradication therapy for H. pylori include (1) monotherapy represented by amoxicillin, (2) classic triple therapy typically using the combination of a bismuth preparation, metronidazole and tetracycline, (3) dual therapy using a proton pump inhibitor and an antibiotic in combination, and (4) new triple therapy consisting of dual therapy plus an antibiotic, by using proton pump inhibitor and two kinds of antibiotics. However, these therapies are associated with many problems in terms of utility, side effects, emergence of resistant strains and compliance, and there has not been established a safe and reliable bacterial eradication therapy. In addition, since many are combined therapies, the dose and administration period of the drugs have not been necessarily consistent. This explains difference in bacterial eradication rates that varied depending on the organizations that enforced the investigation.

Taking note of the superior antibacterial property of new quinolone compounds, there have been recently reported extended application as an anti-H. pylori drug of available levofloxacin, and antibacterial activity of trovafloxacin (34th ICAAC (Orlando, USA): F-24, 1994) and DU-6859a (33rd ICAAC (New Orleans, USA): Abstr. 1188, 1993) against H. pylori.

In these studies in vitro antibacterial activity against H. pylori and in vivo bacterial eradication effect do not always correlate, and they have not amounted to the establishment of a safe and reliable bacterial eradication treatment.

In view of the above, there is a demand for a pharmaceutical agent having superior anti-H. pylori activity in vitro and superior bacterial eradication of H. pylori in vivo, which is useful for the eradication of H. pylori from the patients with gastritis/peptic ulcer, for the treatment of gastritis/peptic ulcer or for the prevention of recurrence/relapse thereof.

DISCLOSURE OF THE INVENTION

The present inventors have conducted intensive studies in an attempt to achieve the above-mentioned objects and found that the compound of the present invention has superior in vitro antibacterial activity against the genus Helicobacter and shows superior in vivo bacterial eradication effect in animal models, such that the compound is useful for the prophylaxis and treatment of the diseases caused by Helicobacter infections, namely, gastritis, gastric ulcer, duodenal ulcer, gastric malignant lymphoma and gastric cancer, which resulted in the completion of the present invention.

The compound of the present invention is effective even when used alone in a small dose for a short time, shows effect against the resistant strains to other antibiotics such as amoxicillin and clarithromycin, is almost free of problematic side effects such as tolerance to the compound of the present invention itself and diarrhea, and is low toxic and capable of safe and reliable bacterial eradication.

In addition, the compound of the present invention shows superior physicochemical properties with excellent stability (e.g, photosensitive stability).

Moreover, the compound of the present invention shows more superior bacterial eradication effect by co-treatment with the antisecretory drugs, and an antibiotic or antiprotozoal drug, as seen in a two-agent or three-agent combined therapy, and is useful for the prophylaxis and treatment of diseases caused by Helicobacter infections, particularly, gastritis, gastric ulcer, duodenal ulcer, gastric malignant lymphoma and gastric cancer, or for the prevention of recurrence or relapse thereof.

Accordingly, the present invention provides the following.

(1) An agent for the prophylaxis or treatment of a disease caused by Helicobacter infections, which comprises (S)-1-cyclopropyl-1,4-dihydro-7-[2-(N,N-dimethylaminomethyl)morpholino]-6-fluoro-8-methoxy-4-oxoquinoline-3-carboxylic acid or a pharmaceutically acceptable salt thereof.

(2) The agent of (1) above, wherein the disease caused by the Helicobacter infections is gastritis, gastric ulcer or duodenal ulcer.

(3) The agent of (1) above, wherein the disease caused by the Helicobacter infections is gastric malignant lymphoma or gastric cancer.

(4) The agent of any of (1) to (3) above, wherein the agent is used in combination with an antisecretory drug.

(5) The agent of (4) above, wherein the agent is used in combination with an antibiotic or antiprotozoal drug.

(6) Use of (S)-1-cyclopropyl-1,4-dihydro-7-[2-(N,N-dimethylaminomethyl)morpholino]-6-fluoro-8-methoxy-4-oxoquinoline-3-carboxylic acid or a pharmaceutically acceptable salt thereof for the production of an agent for the prophylaxis or treatment of a disease caused by Helicobacter infections.

(7) The use of (6) above, wherein the disease caused by the Helicobacter infections is gastritis, gastric ulcer or duodenal ulcer.

(8) The use of (6) above, wherein the disease caused by the Helicobacter infections is gastric malignant lymphoma or gastric cancer.

(9) A method for the prophylaxis or treatment of a disease caused by Helicobacter infections, which comprises administering an effective amount of (S)-1-cyclopropyl-1,4-dihydro-7-[2-(N,N-dimethylaminomethyl)morpholino]-6-fluoro-8-methoxy-4-oxoquinoline-3-carboxylic acid or a pharmaceutically acceptable salt thereof to a patient.

(10) The method of (9) above, wherein the disease caused by the Helicobacter infections is gastritis, gastric ulcer or duodenal ulcer.

(11) The method of (9) above, wherein the disease caused by the Helicobacter infections is gastric malignant lymphoma or gastric cancer.

(12) The method of any of (9) to (11) above, further comprising using an antisecretory drug in combination.

(13) The method of (12) above, further comprising using an antibiotic or antiprotozoal drug in combination.

(14) A commercial package comprising the agent of any of (1) to (3) above, and a written matter associated therewith, the written matter stating that the agent can or should be used for the prophylaxis or treatment of a disease caused by Helicobacter infections.

(15) (S)-1-Cyclopropyl-1,4-dihydro-7-[2-(N,N-dimethylaminomethyl)morpholino]-6-fluoro-8-methoxy-4-oxoquinoline-3-carboxylic acid or a pharmaceutically acceptable salt thereof.

DETAILED DESCRIPTION OF THE INVENTION

The action of the compound of the present invention on the disease caused by Helicobacter infections can be confirmed basd on the superior in vitro antibacterial activity against *H. pylori*, and superior in vivo bacterial eradication in animal models.

The genus Helicobacter includes bacteria such as *H. pylori, H. heilmanii, H. felis, H. hepaticus* and the like.

By the disease caused by Helicobacter infections is meant any disease caused by infection with any of the above-mentioned bacteria belonging to the genus Helicobacter. Examples thereof include gastritis, gastric ulcer, duodenal ulcer, malignant lymphoma and gastric cancer. In the present invention, the prophylaxis and treatment of the diseases caused by Helicobacter infections encompass prophylaxis and treatment of these diseases and prevention of recurrence and relapse thereof.

The compound of the present invention is optically active and can be synthesized according to a conventional method described in JP-A-3-7283. More particularly, it can be synthesized according to the method disclosed in the following Starting Material Preparation Example and Example.

The pharmaceutically acceptable salt of the compound of the present invention includes acid addition salts of hydrochloric acid, hydrobromic acid, hydroiodic acid, sulfuric acid, nitric acid, phosphoric acid, acetic acid, citric acid, maleic acid, fumaric acid, malonic acid, malic acid, tartaric acid, succinic acid, methanesulfonic acid, benzenesulfonic acid and the like, alkaline metal salts such as sodium, potassium and the like, alkaline earth metal salts such as calcium, magnesium and the like, heavy metal salts such as copper, zinc, iron, gold, platinum, manganese and the like, and the like. The compound of the present invention can exist as hydrates (semihydrate, monohydrate, sesquihydrate and the like) and solvates, which are also encompassed in the present invention.

When the compound of the present invention is used as a medicament, the compound of the present invention can be administered orally or parenterally in the form of tablet, pill, capsule, granule, powder, syrup, emulsion, elixir, suspension, solution, injection, infusion, suppository and the like, that are obtained by formulating a pharmaceutical composition according to a conventional method, wherein the composition is prepared by mixing with a pharmaceutically acceptable carrier (e.g., excipient, binder, disintegrator, corrective, corrigent, emulsifier, diluent, solubilizer and the like).

In the present specification, by parenteral is meant subcutaneous injection, intravenous injection, intramuscular injection, intraperitoneal injection, infusion and the like. An injectable preparation such as sterile injectable aqueous suspension or oily suspension can be prepared by the use of a suitable dispersing agent or wetting agent and suspending agent according to the method known in the pertinent field. Such sterile injectable preparation may be a non-toxic parenterally administerable diluent, such as an aqueous solution and the like, or a sterile injectable solution or suspension in a solvent. Usable vehicle or solvent may be, for example, water, Ringer solution, isotonic brine and the like. As a solvent or a suspending solvent, sterile nonvolatile oil can be also used. Any nonvolatile oil or fatty acid can be used for this end, which includes natural or synthetic or semi-synthetic fatty oil or fatty acid, natural or synthetic or semi-synthetic mono- or di- or triglycerol. The suppository for rectal administration can be prepared by mixing the drug with a suitable non-irritative base, such as cocoa butter and polyethyleneglycol, that are solid at ordinary temperature, liquid at the temperature in the intestinal tract, and melts in rectum to release the drug.

The solid dosage form for oral administration is exemplified by those mentioned above, such as powder, granule, tablet, pill, capsule and the like. In such dosage form, the active ingredient compound can be admixed with at least one additive, such as sucrose, lactose, cellulose sugar, mannitol, maltitol, dextran, starch, agar, arginate, chitin, chitosan, pectin, tragacanth gum, gum arabic, gelatin, collagen, casein, albumin, synthetic or semi-synthetic polymer and glyceride. Such dosage form can contain further additives as usual, such as inactive diluent, lubricant (e.g., magnesium stearate and the like), preservative (e.g., p-hydroxybenzoate, sorbate and the like), antioxidant (e.g., ascorbic acid, α-tocopherol, cysteine and the like), disintegrator, binder, tackifier, buffer, sweetener, flavor, perfume and the like. Tablets and pills may be further enteric coated. Liquid preparation for oral administration include, for example, pharmaceutically acceptable emulsion, syrup, elixir, suspension, solution and the like, which may contain inactive diluent typically used in this field, such as water.

The dose is determined according to age, body weight, general health conditions, sex, diet, administration time, administration route, clearance rate, combination of drugs, the disease state for which the patient is under treatment, and other factors. The compound of the present invention and a pharmaceutically acceptable salt are low toxic and can be used safely. While the daily dose varies depending on the condition and body weight of patient, the kind of compound, administration route and the like, it is about 0.1–10 mg/kg adult patient/day, and preferably 0.5–2 mg/kg adult patient/day, by oral administration. It is needless to say the dose is subject to change depending on the condition, age, drug resistance and the like of the patient.

The compound of the present invention shows more superior bacterial eradication effect by co-treatment with an antisecretory drug, and an antibiotic or antiprotozoal drug, as seen in a dual or triple therapy. The compound of the present invention is expected to show enhanced prophylactic and therapeutic effect on the diseases caused by Helicobacter infections.

The concurrent use is subject to no particular limitation as to the mode of administration, as long as the effect of each drug is ultimately exerted in collaboration in the body, and, for example, a preparation simultaneously containing two or three agents may be administered, or alternatively, the two or three agents may be administered separately to achieve this effect.

The antisecretory drug to be used in the present invention may be, for example, proton pump inhibitor, histamine $H_2$ antagonist and the like. Examples of the proton pump inhibitor include omeprazole, lansoprazole, pantoprazole, rabeprazole and the like.

Examples of the histamine $H_2$ antagonist include cimetidine, ranitidine, famotidine, roxatidine and the like.

The medicament of the present invention may contain the compound of the present invention, an antisecretory drug and an antibiotic or an antiprotozoal drug.

Examples of the antibiotics include antibiotics, such as amoxicillin, clarithromycin, ampicillin, prodrugs thereof and the like.

Examples of the antiprotozoal drug include metronidazole, tinidazole and the like.

These drugs preferably are commercially available.

The dose of the drugs to be concurrently used with the compound of the present invention is appropriately determined depending on the kind of disease and symptoms, wherein an antisecretory drug is administered at 0.01–10 mg/kg/day, preferably 0.1–1.0 mg/kg/day, an antibiotic at 0.1–100 mg/kg/day, preferably 5–30 mg/kg/day, and an antiprotozoal drug at 0.1–100 mg/kg/day, preferably 1–10 mg/kg/day.

EXAMPLES

The present invention is explained in more detail in the following by way of Starting Material Preparation Examples, Example, Formulation Examples and Pharmacological Experimental Examples, that do not limit the present invention in any way.

The compound of the present invention can be synthesized by the following method.

Starting Material Preparation Example 1

(RS)-2-Aminomethyl-4-benzylmorpholine (326.1 g) was dissolved in ethanol (3 L) and dibenzoyl-D-tartaric monohydrate (535 g) was added. The mixture was refluxed for dissolution and then left standing at room temperature for 16 hours. The precipitated crystals were collected by filtration and recrystallized from a mixed solvent of ethanol:water= 25:1. The obtained crystals were suspended in water (1.2 L) and aqueous sodium hydroxide solution was added with stirring to make the suspension basic, which was followed by extraction with chloroform. The chloroform layer was dried over anhydrous magnesium sulfate and the solvent was distilled off to give 138.4 g of (S)-2-aminomethyl-4-benzylmorpholine as a colorless oil.

$[\alpha]_D$=−25.3° (c=1%, MeOH)

$^1$H-NMR(CDCl$_3$): δ(ppm)=1.20(s,2H), 1.87 (dd, 1H), 2.10–2.20 (m, 1H), 2.62–2.75 (m, 4H), 3.43–3.53 (m, 3H), 3.62–3.71 (m, 1H), 3.83–3.89 (m, 1H), 7.22–7.31 (m, 5H)

Starting Material Preparation Example 2

(S)-2-Aminomethyl-4-benzylmorpholine (138.4 g) was added to formic acid (185.2 g) under ice-cooling and the mixture was heated to 70° C. Aqueous 37% formaldehyde solution (119.5 g) was added dropwise and the mixture was stirred at 75–80° C. for 1 hour. After cooling, sodium hydroxide (124 g) dissolved in water (460 ml) was added and the mixture was extracted with toluene. The toluene layer was dried over anhydrous magnesium sulfate and the solvent was distilled off to give a pale-yellow oil. The oil was distilled off under reduced pressure (120° C., 0.4 mmHg) to give 78.9 g of (S)-4-benzyl-2-(N,N-dimethylaminomethyl)morpholine as a colorless oil.

$[\alpha]_D$=−31.0° (c=1%, MeOH)

$^1$H-NMR(CDCl$_3$): δ(ppm)=1.86 (dd, 1H), 2.11–2.20 (m, 2H), 2.49 (dd, 1H), 2.67–2.76 (m, 2H), 3.44–3.55 (m, 2H), 3.66–3.71 (m, 2H), 3.84–3.86 (m, 1H), 7.25–7.32 (m, 5H)

Starting Material Preparation Example 3

(S)-4-Benzyl-2-(N,N-dimethylaminomethyl)morpholine (78.9 g) was dissolved in ethanol (800 ml) and 10% palladium carbon (31.1 g) and hydrazine monohydrate (22.1 g) were added with stirring at room temperature. The mixture was refluxed with stirring for 1 hour. After cooling, the reaction mixture was filtered through celite and the solvent was distilled off to give 42.8 g of (R)-2-(N,N-dimethylaminomethyl)morpholine as a pale-yellow oil.

$[\alpha]_D$=−15.2° (c=1%, CHCl$_3$)

$^1$H-NMR(CDCl$_3$): δ(ppm)=1.77 (s, 1H), 2.15 (dd, 1H), 2.26 (s, 6H), 2.38–2.57 (m, 2H), 2.81–2.87 (m, 3H), 3.56–3.63 (m, 2H), 3.86–3.92 (m, 1H)

Example 1

(R)-2-(N,N-Dimethylaminomethyl)morpholine (42.3 g) was dissolved in acetonitrile (1 L) and 1-cyclopropyl-6,7-difluoro-1,4-dihydro-8-methoxy-4-oxoquinoline-3-carboxylic acid BF$_2$ chelate (100.8 g) and triethylamine (31.2 g) were added. The mixture was stirred at room temperature for 15 hours and heated to 40–55° C. and stirred for 2 hours. After cooling, the solvent was distilled off and the obtained orange red oil was dissolved in methanol (1 L) and triethylamine (250 ml) was added, which was followed by refluxing with stirring for 2.5 hours. After cooling, the solvent was distilled off and the residue was suspended in 1N hydrochloric acid (1 L), washed with ethyl acetate, made alkaline with potassium carbonate and washed with ethyl acetate. The aqueous layer was neutralized with acetic acid and extracted with chloroform. The chloroform layer was dried over anhydrous magnesium sulfate and the solvent was distilled off to give a brown oil. The oil was dissolved in isopropanol. Isopropyl ether was added and the precipitated crystals were collected by filtration. The crystals were recrystallized from isopropanol to give 48.0 g of (S)-1-cyclopropyl-1,4-dihydro-7-[2-(N,N-dimethylaminomethyl) morpholino]-6-fluoro-8-methoxy-4-oxoquinoline-3-carboxylic acid as pale-yellow crystals, melting point 146–147° C.

$[\alpha]_D = -6.3°$ (c=1%, $CHCl_3$) (hereinafter the compound of the present invention is referred to as Y-34867)

The medicament of the present invention is formulated, for example, as in the following.

Formulation Example 1

Tablet: Tablets containing 100 mg of the active ingredient are prepared to have the following composition.

| | |
|---|---|
| Y-34867 | 100 mg |
| Corn starch | 45 mg |
| Lactose | 170 mg |
| Microcrystalline cellulose | 75 mg |
| Magnesium stearate | 10 mg |
| | 400 mg |

Formulation Example 2

Capsule: Capsules containing 100 mg of the active ingredient are prepared to have the following composition.

| | |
|---|---|
| Y-34867 | 100 mg |
| Corn starch | 90 mg |
| Lactose | 190 mg |
| Hydroxypropylcellulose | 17 mg |
| Magnesium stearate | 3 mg |
| | 400 mg |

Pharmacological Experimental Example 1

In Vitro Antibacterial Activity Against *H. pylori*

Clinically isolated strains (18 strains) were cultured using 5% horse serum under microaerophilic conditions at 37° C. for 72 hours and diluted with Brucella broth to give a bacterial solution at about $10^6$ cells/ml. The diluted bacterial solution was inoculated with a microplanter on an agar plate containing 2-fold dilution concentration series of test compound and cultured under 8% $CO_2$ at 37° C. for 3 to 4 days. Thereafter, the minimum growth inhibitory concentration (MIC) was measured. $MIC_{50}$ (minimum concentration to inhibit growth in 50% of the test strains) and $MIC_{90}$ (minimum concentration to inhibit growth in 90% of the test strains) were calculated from the obtained values.

As a result, the compound of the present invention showed $MIC_{50}$ and $MIC_{90}$ of 0.025 µg/ml and 0.05 µg/ml, respectively.

Pharmacological Experimental Example 2

To a male 7-week-old Mongolian gerbil after fasting for about 20 hours, was inoculated orally a culture broth of *H. pylori* ATCC 43504 Type strain upon 24 hours of culture. After administration of the culture broth, the Mongolian gerbil was fasted and deprived of water for about 4 hours, after which a normal solid feed and drinking water were given to Mongolian gerbils infected with *H. pylori*. Starting from 6 weeks after infection, the drug was orally administered twice a day for 7 days. After completion of the drug administration, Mongolian gerbils were sacrificed at day 3. The stomach was excised and incised along greater curvature, and its content was removed. The stomach was homogenized in 10 ml of phosphate buffer—physiological saline in a homogenizer. The homogenate was appropriately diluted with the same buffer and 0.1 ml of sample was plated onto *H. pylori* selective medium. The medium was incubated under $CO_2$ and the colonies of *H. pylori* were counted. A case where colonies were not detected was evaluated as the case of bacterial eradication. The results are shown in Table 1.

TABLE 1

| Compound | MIC (µg/ml) | Dose (mg/kg, bid) | Eradication rate (%) |
|---|---|---|---|
| Y-34867 | 0.025 | 0.3 | 0(0/5) |
| | | 1.0 | 80(4/5) |
| | | 3.0 | 100(5/5) |
| amoxicillin | 0.025 | 3.0 | 0(0/5) |
| | | 10.0 | 100(5/5) |

The compound of the present invention showed evident bacterial eradication of *H. pylori*, and promoted visual and histopathological repair of inflammatory state.

Pharmacological Experimental Example 3

To a male 7-week-old Mongolian gerbil after fasting for about 20 hours, was inoculated orally a culture broth of *H. pylori* ATCC 43504 Type strain upon 24 hours of culture. After administration of the culture broth, the Mongolian gerbil was fasted and deprived of water for about 4 hours, after which a normal solid feed and drinking water were given to Mongolian gerbils infected with *H. pylori*. Starting from 6 weeks after infection, the compound of the present invention and famotidine which is a histamine $H_2$ antagonist were administered alone or in combination twice a day for 3 days. The compound of the present invention was administered orally and famotidine was subcutaneously administered immediately before administration of the compound of the present invention. After completion of the drug administration, Mongolian gerbils were sacrificed at day 3. The stomach was excised and incised along greater curvature and its content was removed. The stomach was homogenized in 10 ml of phosphate buffer—physiological saline. The homogenate was appropriately diluted with the same buffer and 0.1 ml of sample was inoculated onto *H. pylori* selective medium. The medium was incubated under $CO_2$ and the colonies of *H. pylori* were counted. A case where colonies were not detected was evaluated as the case of bacterial eradication. As a control, phosphate buffer—physiological saline was used. The results are shown in Table 2.

TABLE 2

| Compound | Dose (mg/kg, bid) | Eradication rate (%) |
|---|---|---|
| Control | — | 0(0/5) |
| Y-34867 | 0.3 | 0(0/5) |
| (oral administration) | 1.0 | 60(3/5) |
| | 3.0 | 100(5/5) |
| Y-34867 + famotidine | 0.3 + 100 | 100(5/5) |

TABLE 2-continued

| Compound | Dose (mg/kg, bid) | Eradication rate (%) |
| --- | --- | --- |
| | 1.0 + 100 | 100(5/5) |
| | 3.0 + 100 | 100(5/5) |
| famotidine (subcutaneous administration) | 100 | 0(0/5) |

The compound of the present invention shows superior bacterial eradication effect by single administration, but the effect is enforced when concurrently administered with famotidine, which is a histamine $H_2$ antagonist, thereby enabling bacterial eradication in a short time at a small dose. In addition, visual and histopathological repair of inflammatory state was promoted. The incidence of relapse of inflammatory symptom was not observed in the group evaluated to be a completely eradicated group. The drug used in combination is not particularly limited to famotidine but agents other than famotidine, such as an antisecretory drug (e.g., histamine $H_2$ antagonist, proton pump inhibitor and the like), an antibiotic and an antiprotozoal drug can be also used in combination.

Industrial Applicability

The compound of the present invention and a pharmaceutically acceptable salt thereof have superior in vitro antibacterial activity against *H. pylori*, superior in vivo bacterial eradication action in animal models, and the like, as shown in the above-mentioned pharmacological experimental examples and the like, such that they are useful for the prophylaxis and treatment of diseases caused by Helicobacter infections, particularly, gastritis, gastric ulcer, duodenal ulcer, malignant lymphoma and gastric cancer, in mammals inclusive of human, or for the prevention of recurrence or relapse thereof.

The compound of the present invention is effective even when used alone in a small dose for a short time, shows effect against bacteria resistant to other antibiotics such as amoxicillin and clarithromycin, is almost free of tolerance to the compound of the present invention itself or problematic side effects such as diarrhea and is low toxic, and capable of safe and reliable bacterial eradication.

In addition, the compound of the present invention shows superior physicochemical properties with excellent stability (e.g, photosensitive stability).

Moreover, the compound of the present invention shows more superior bacterial eradication effect by co-treatment use with an antisecretory drug, and an antibiotic or antiprotozoal drug, as seen in a dual or triple therapy, and is useful for the prophylaxis and treatment of diseases caused by Helicobacter infections, particularly, gastritis, gastric ulcer, duodenal ulcer, gastric malignant lymphoma and gastric cancer, or for the prevention of recurrence or relapse thereof.

This application is based on application No. 165646/1997 filed in Japan, the content of which is incorporated hereinto by reference.

What is claimed is:

1. An agent for the prophylaxis or treatment of a disease caused by Helicobacter infections, which comprises (S)-1-cyclopropyl-1,4-dihydro-7-[2-(N,N-dimethylaminomethyl)morpholino]-6-fluoro-8-methoxy-4-oxoquinoline-3-carboxylic acid or a pharmaceutically acceptable salt thereof, and an antisecretory drug.

2. The agent of claim 1 which further comprises an antibiotic or antiprotozoal drug.

3. A method for the prophylaxis or treatment of a disease caused by Helicobacter infections, which comprises administering an effective amount of (S)-1-cyclopropyl-1,4-dihydro-7-[2-(N,N-dimethylaminomethyl)morpholino]-6-fluoro-8-methoxy-4-oxoquinoline-3-carboxylic acid or a pharmaceutically acceptable salt thereof to a patient.

4. The method of claim 3, wherein the disease caused by the Helicobacter infections is gastritis, gastric ulcer or duodenal ulcer.

5. The method of claim 3, wherein the disease caused by the Helicobacter infections is gastric malignant lymphoma or gastric cancer.

6. The method of any of claim 3 to claim 5, further comprising using an antisecretory drug in combination.

7. The method of claim 6, further comprising using an antibiotic or antiprotozoal drug in combination.

* * * * *

UNITED STATES PATENT AND TRADEMARK OFFICE
CERTIFICATE OF CORRECTION

PATENT NO.     : 6,221,864 B1
DATED          : April 24, 2001
INVENTOR(S)    : Fumihiro Hirayama, Mitsuharu Sano, Nobuhiro Sakurai and Yoshito Yokoyama It is certified that error appears in the above-identified patent and that said Letters Patent is hereby corrected as shown below:

<u>Title page,</u>
The following information is added to the heading of the patent:

-- PCT filed:         June 23, 1998
   PCT No.:           PCT/JP98/02790
   § 371 Date:        December 23, 1999
   § 102(e) Date:     December 23, 1999
   PCT Pub No.:       WO 98/58928
   PCT Pub. Date:     December 30, 1998 --

Signed and Sealed this

Eighteenth Day of June, 2002

*Attest:*

*Attesting Officer*

JAMES E. ROGAN
*Director of the United States Patent and Trademark Office*